(12) United States Patent
Asgharian et al.

(10) Patent No.: US 6,228,323 B1
(45) Date of Patent: May 8, 2001

(54) MULTI-PURPOSE COMPOSITIONS CONTAINING AN ALKYL-TRYPSIN AND METHODS OF USE IN CONTACT LENS CLEANING AND DISINFECTING

(75) Inventors: Bahram Asgharian; Bor-Shyue Hong, both of Arlington, TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/144,673

(22) Filed: Sep. 1, 1998

Related U.S. Application Data

(63) Continuation-in-part of application No. PCT/US97/21579, filed on Nov. 24, 1997.
(60) Provisional application No. 60/032,839, filed on Dec. 13, 1996, now abandoned.

(51) Int. Cl.[7] .................................................. A61L 2/00
(52) U.S. Cl. ...................... 422/28; 252/106; 424/94.1; 424/94.3; 424/264; 435/264
(58) Field of Search ................... 422/28; 424/94.1, 424/94.3, 264; 435/264; 252/106

(56) References Cited

U.S. PATENT DOCUMENTS

| | | |
|---|---|---|
| Re. 32,672 | 5/1988 | Huth et al. . |
| 3,402,855 | * 9/1968 | Schroeder et al. ..................... 222/83 |
| 3,613,955 | * 10/1971 | Wetherell, Jr. ......................... 222/83 |
| 3,731,844 | * 5/1973 | Baker ................................. 222/83 X |
| 3,910,296 | 10/1975 | Karageozian et al. . |
| 3,924,741 | * 12/1975 | Kachur et al. ........................ 206/221 |
| 4,407,791 | 10/1983 | Stark . |
| 4,525,346 | 6/1985 | Stark . |
| 4,614,549 | 9/1986 | Ogunbiyi et al. . |
| 4,758,595 | 7/1988 | Ogunbiyi et al. . |
| 4,836,986 | 6/1989 | Ogunbiyi et al. . |
| 5,096,607 | 3/1992 | Mowrey-McKee et al. . |
| 5,281,277 | 1/1994 | Nakagawa et al. . |
| 5,409,546 | 4/1995 | Nakagawa et al. . |
| 5,419,445 | * 5/1995 | Kaesemeyer ..................... 206/220 X |
| 5,421,483 | * 6/1995 | Parise ..................................... 222/82 |

(List continued on next page.)

FOREIGN PATENT DOCUMENTS

| | | |
|---|---|---|
| 1 150 907 | 8/1983 | (CA) . |
| 0 384 666 | 8/1990 | (EP) . |
| 0 456 467 | 11/1991 | (EP) . |
| 0 646 641 | 4/1995 | (EP) . |
| 57-24526 | 5/1982 | (JP) . |
| 92-143718 | 5/1992 | (JP) . |
| 92-243215 | 8/1992 | (JP) . |
| 92-370197 | 12/1992 | (JP) . |
| WO 89/111878 | 12/1989 | (WO) . |
| WO 94/06479 | 3/1994 | (WO) . |
| WO 96/40854 | 12/1996 | (WO) . |
| WO 97/18288 | 5/1997 | (WO) . |
| WO 98/25650 | 6/1998 | (WO) . |

OTHER PUBLICATIONS

Lo, J.; Silverman, H.; and Korb, D.; Studies on cleaning solutions for contact lenses, *Journal of the American Optometric Association*, vol. 40, pp. 1106–1109 (1969).

Means, GE and Feeney, RE. Reductive alkylation of amino groups in proteins, *Biochemistry*, vol. 7, pp. 2192–2201 (1968).

Rice, RH, Means, GE and Brown, WD. Stabilization of bovine trypsin by reductive methylation, *Biochimica et Biophysica Acta*, vol. 492, pp. 316–321 (1977).

*Primary Examiner*—Krisanne Thornton
(74) *Attorney, Agent, or Firm*—Michael C. Mayo

(57) ABSTRACT

Two-compartment bottle assemblies useful in preparing multi-purpose compositions containing an Al-trypsin and disinfectant, methods of preparing these compositions and methods involving the use of these compositions are disclosed for cleaning and disinfecting of contact lenses.

33 Claims, 7 Drawing Sheets

U.S. PATENT DOCUMENTS

| | | |
|---|---|---|
| 5,576,278 | 11/1996 | Van Duzee et al. . |
| 5,604,190 | 2/1997 | Chowhan et al. . |
| 5,605,661 | 2/1997 | Asgharian et al. . |
| 5,672,213 | 9/1997 | Asgharian et al. . |
| 5,718,895 | 2/1998 | Asgharian et al. . |
| 5,723,421 | 3/1998 | Chowhan et al. . |
| 5,785,767 | 7/1998 | Kimura et al. .......................... 134/42 |
| 5,820,696 | 10/1998 | Kimura et al. .......................... 134/42 |

* cited by examiner

US 6,228,323 B1

MULTI-PURPOSE COMPOSITIONS CONTAINING AN ALKYL-TRYPSIN AND METHODS OF USE IN CONTACT LENS CLEANING AND DISINFECTING

This application is a continuation-in-part of patent application Ser. No. PCT/US97/21579, filed Nov. 24, 1997; which claims priority to U.S. Provisional Patent Application Serial No. 60/032,839, filed Dec. 13, 1996, now abandoned.

BACKGROUND OF THE INVENTION

The present invention relates to the field of contact lens cleaning and disinfecting. In particular, this invention is directed to the provision of alkyl trypsin containing multi-purpose compositions and methods for the preparation of these compositions. The invention is also directed to methods of simultaneously cleaning and disinfecting contact lenses by using alkyl trypsin and disinfectant containing multi-purpose compositions of the present invention.

Various compositions and methods for cleaning contact lenses have been described in the patent and scientific literature. Some of these methods have employed compositions containing surfactants or enzymes to facilitate the cleaning of lenses. The first discussion of the use of proteolytic enzymes to clean contact lenses was in an article by Lo, et al. in the *Journal of The American Optometric Association*, volume 40, pages 1106–1109 (1969). Methods of removing protein deposits from contact lenses by means of proteolytic enzymes have been described in many publications since the initial article by Lo, et al., including U.S. Pat. No. 3,910,296 (Karageozian, et al.).

Numerous compositions and methods for disinfecting contact lenses have also been described. Those methods may be generally characterized as involving the use of heat and/or chemical agents. Representative chemical agents for this purpose include organic anti-microbials such as benzalkonium chloride and chlorhexidine, and inorganic antimicrobials such as hydrogen peroxide and peroxide-generating compounds. U.S. Pat. Nos. 4,407,791 and 4,525,346 (Stark) describe the use of polymeric quaternary ammonium compounds to disinfect contact lenses and to preserve contact lens care products. U.S. Pat. Nos. 4,758,595 and 4,836,986 (Ogunbiyi) describe the use of polymeric biguanides for the same purpose.

Various methods for enzymatic cleaning and disinfecting contact lenses at the same time have been proposed. Methods involving the combined use of proteolytic enzymes and peroxides to clean and disinfect contact lenses simultaneously, are described in U.S. Pat. No. Re 32,672 (Huth, et al.). A representative method of simultaneously cleaning and disinfecting contact lenses involving the use of proteolytic enzymes and quaternary ammonium compounds is described in Japanese Patent Publication 57-24526 (Boghosian, et al.). The combined use of a biguanide (i.e., chlorhexidine) and liquid enzyme compositions to simultaneously clean and disinfect contact lenses is described in Canadian Patent No. 1,150,907 (Ludwig, et al.). Methods involving the combined use of dissolved proteolytic enzymes to clean and heat to disinfect are described in U.S. Pat. No. 4,614,549 (Ogunbiyi). The combined use of proteolytic enzymes and polymeric biguanides or polymeric quaternary ammonium compounds is described in copending, commonly assigned U.S. patent application Ser. No. 08/156,043 and in corresponding European Patent Application Publication No. 0 456 467 A2 (Rosenthal, et al.), as well as in U.S. Pat. No. 5,096,607 (Mowrey-McKee, et al.).

The commercial viability of most prior enzymatic cleaning products has depended on the use of stable enzyme tablets. More specifically, the use of solid enzymatic cleaning compositions has been necessary to ensure stability of the enzymes prior to use. In order to use such compositions, a separate packet containing a tablet must be opened, the tablet must be placed in a separate vial containing a solution, and the tablet must be dissolved in order to release the enzyme into the solution. This practice is usually performed only once a week due to the cumbersome and tedious procedure and potential for irritation and toxicity.

The use of concentrated liquid enzyme compositions in combination with a diluent to clean contact lenses has been attempted in an effort to avoid the cumbersome use of enzyme tablets. Those attempts, however, have been hampered by the fact that concentrated aqueous liquid enzyme compositions are inherently unstable. When a proteolytic enzyme is placed in an aqueous solution for an extended period (i.e., several months or more), the enzyme may lose all or a substantial portion of its proteolytic activity. Steps can be taken to stabilize the compositions. For example, stabilizing agents can protect enzymes from chemical instability problems during storage in an aqueous liquid, by placing the enzymes in a dormant physical conformation. However, the use of liquid enzyme compositions, as with the use of enzyme tablet compositions described above, still requires a separate, additional mixing step each time the lens is to be simultaneously cleaned and disinfected. Furthermore, since the amount of liquid enzyme composition placed in a diluting composition is controlled by the user, user error may result in too much or too little of the concentrate being dispensed in the diluting solution.

The following patents may be referred to for further background concerning prior attempts to stabilize concentrated liquid enzyme formulations: U.S. Pat. No. 5,281,277 (Nakagawa) and Japanese Kokai Patent Applications Nos. 92-370197; 92-143718; and 92-243215. Improved liquid enzyme compositions have been disclosed in U.S. Pat. Nos. 5,576,278, 5,604,190, 5,605,661, 5,672,213 5,718,895 and 5,723,421, all issued to Alcon Laboratories, Inc.

A number of multi-purpose compositions for cleaning, disinfecting and storing contact lenses are commercially available. The main cleaning ingredients of these products generally comprise surfactants. Soft contact lenses become soiled by collecting various debris and also by accumulated protein deposition on the lens surface. Failure to remove the protein deposits results in opacification of the lens and lens spoilage. While surfactants are used to remove debris from the lens, they are not very efficacious in removing protein deposits. Proteolytic agents, in contrast, are very effective in removing protein deposits that form on the lens over time. Thus, cleaning regimens using multi-purpose compositions comprising surfactants still require the additional step of employing a proteolytic agent to remove protein deposits.

The use of a single enzyme containing multi-purpose solution for the cleaning and disinfecting of contact lenses has been proposed in U.S. Pat. No. 5,409,546 (Nakagawa et al.) and European Patent Application No. 0 646, 641 (Nakagawa et al.). Those patents disclose compositions wherein the enzyme is in a dilute concentration, and the compositions, therefore, require no dilution step prior to use. Those compositions, however, provide limited stability of the enzyme (1 or 2 months at room temperature). The limited shelf-life of these compositions generally does not permit their commercialization.

What is needed, therefore, are multi-purpose compositions which provide a commercially viable storage/use shelf-life.

SUMMARY OF THE INVENTION

Figure 1:
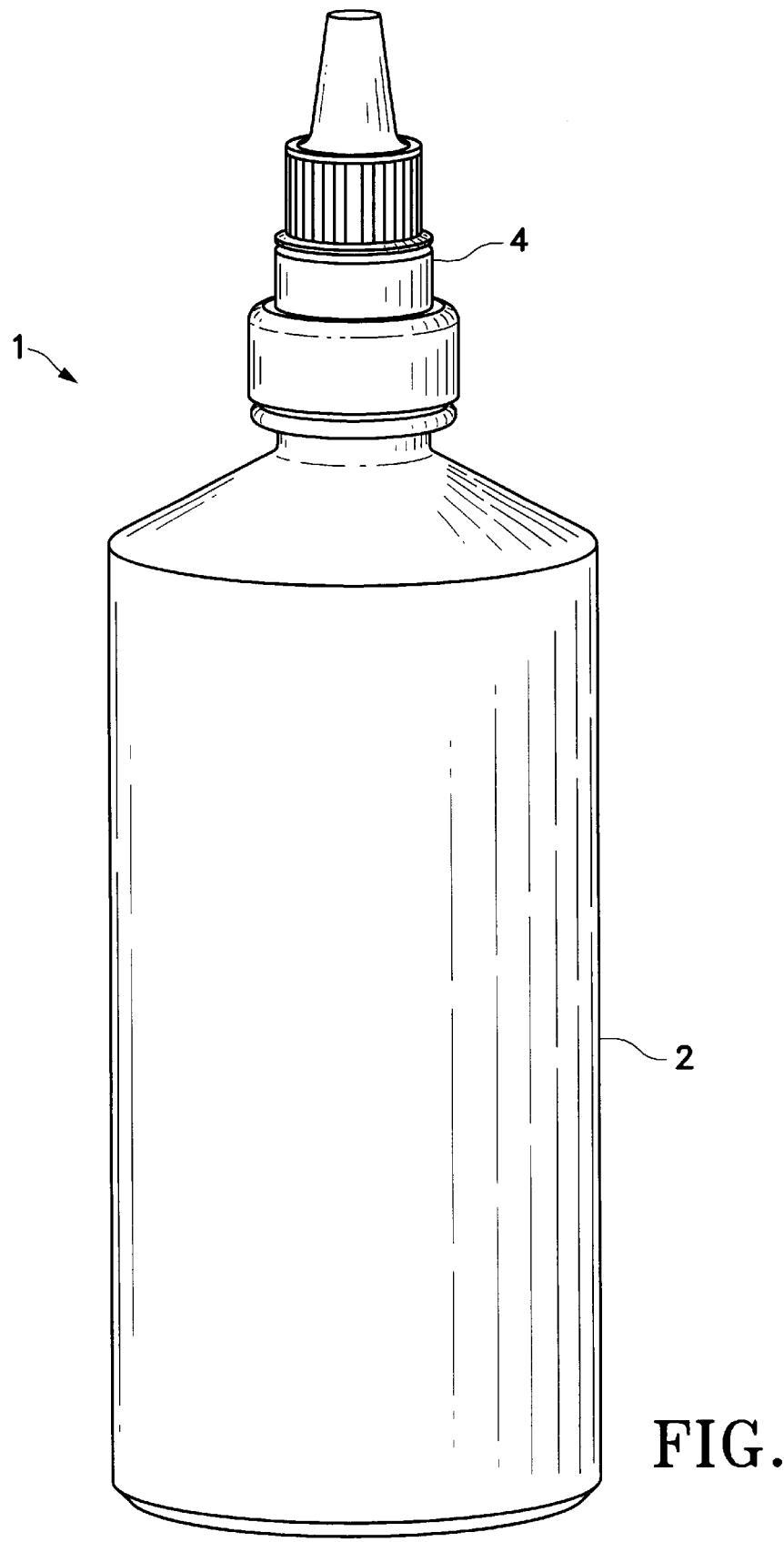
FIG. 1 is a perspective view of a preferred embodiment of the invention.

The present invention is directed to two-part systems which provide for the generation of multi-purpose compositions useful in the simultaneous cleaning and disinfecting of contact lenses. The present invention is also directed to stable multi-purpose compositions. The present invention is further directed to methods of simultaneously cleaning and disinfecting contact lenses using the two-part system. The two-part system comprises an alkyl trypsin ("Al-trypsin") cleaning composition, an aqueous composition and one or more anti-microbial agent(s). The Al-trypsin composition provides a concentrated amount of an Al-trypsin. The aqueous composition provides a diluting solution. The anti-microbial agent is contained in either the Al-trypsin composition or the aqueous composition. The two-part system is initialized for use by admixing the Al-trypsin composition with the aqueous composition.

The two-part system uses a two-compartment device capable of keeping separate an enzyme composition and a diluting composition prior to their initial use. One feature of this device is that it combines the separate components in a single bottle assembly. This feature has the advantage over prior art systems which have required the more difficult, tedious and cumbersome use of separate containers. Related to this feature is the fact that the enzyme is added only once to the disinfecting composition, and the resulting multi-purpose composition can then be used many times over a period of several months. With most prior art systems, the enzyme must be added to the disinfecting composition each time the user cleans his lenses. A further advantage of this feature is that the two compositions are admixed is aseptically. This is due to the fact that the bottle assembly containing the two compositions is assembled in an aseptic manner with an air-tight seal, thus sterile mixing is performed within the closed sterile system of the bottle assembly. Still another advantage of this feature is that it eliminates possible user error resulting from the addition of improper amounts of an enzyme composition to the diluting solution. This is important as improper amounts of enzymes or excipients (e.g., salts) in the resultant multi-purpose solution can lead to ineffective cleaning and disinfecting of the lens and/or ocular toxicity. Thus, user compliance with the cleaning regimen is perfected with the present invention, allowing for the realization of maximum cleaning benefits, and the avoidance of unnecessary ocular irritation/toxicity.

Another feature of the present invention is that the Al-trypsin component is kept separate from the diluting solution prior to initial use. This feature minimizes enzyme activity loss, which naturally occurs over time in aqueous environments, by minimizing the time the enzyme is solubilized in the diluent prior to initial use. This feature allows for ambient temperature shipping, and long shelf-life without significant loss of enzyme activity. When the user is ready to use the system, the two components are combined and mixed aseptically, forming the multi-purpose composition. The multi-purpose composition can then be used for a period of from about 1–3 months.

Another feature of the present invention is the employment of an Al-trypsin as the cleaning agent in the compositions. Al-trypsins have been discovered to possess superior stability in liquid concentrated and diluted multi-purpose solutions. Thus, the use of an Al-trypsin in the present invention compositions provides prolonged pre-mixed storage, as well as extended stability for the post-mixed, ready-to-use multi-purpose compositions of the present invention.

The cleaning and disinfecting compositions of the present invention may utilize ingredients similar to known cleaning or disinfection formulations. Various modifications may be made, however, to enhance the anti-microbial efficacy of the multi-purpose composition. Other additional components may also be added to enhance the shelf-life of the mixed components, such as the use of enzyme stabilizers.

The multi-purpose compositions and methods of the present invention provide greater ease of use. This ease of use enables contact lens users to clean their lenses daily, thereby achieving maximum proteolytic cleaning of their lenses. It has been found that daily use of a liquid enzyme cleaner results in dramatically better cleaning, as compared to the once-a-week enzyme cleaning regimens currently being used.

DETAILED DESCRIPTION OF THE INVENTION

The present invention is directed to the use of a sterile two-part system for the preparation of multi-purpose compositions useful for cleaning and disinfecting contact lenses. The present invention is also directed to stable, multi-purpose compositions. The present invention is also directed to methods of cleaning and disinfecting contact lenses by using the two-part systems. The first part ("Part I") is a sterile Al-trypsin containing solid (powder or tablet) or liquid composition and the second part ("Part II") is a sterile diluting composition. An anti-microbial agent is further required, and may be included in either composition.

The present invention two-part systems require the use of a two-compartment device to store and mix the sterile two-part system, and to dispense the resultant sterile multi-purpose composition. Various devices may be employed, but the central features of the device are that it provides separate component storage, a means for aseptically adding one component to the other component, a mixing chamber and a dispensing means, all in a single bottle assembly.

FIG. 1 illustrates a preferred two-part bottle assembly for use with the two-part/multi-purpose compositions of the present invention. The preferred two-part bottle assembly, bottle assembly 1, generally comprises bottle 2 and container 4.

Figure 2:
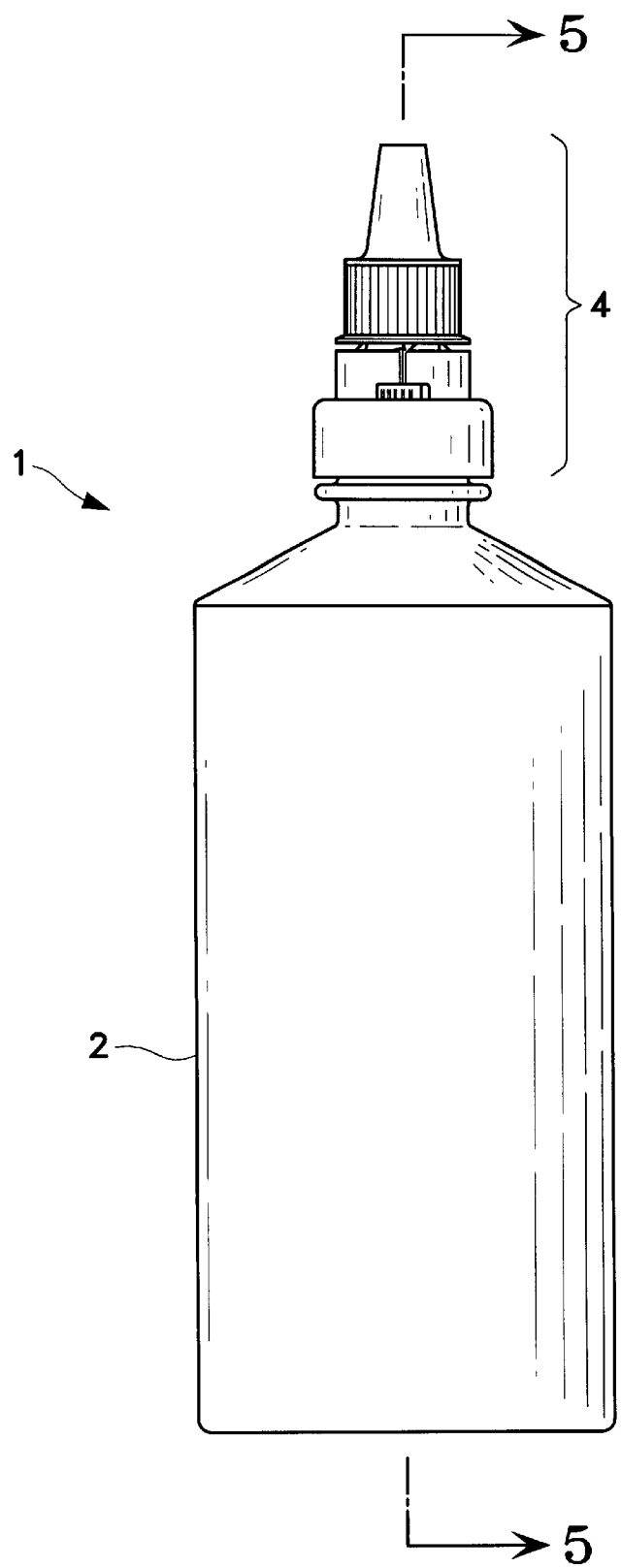
FIG. 2 is an elevation view of a preferred embodiment of the invention.
Figure 3:
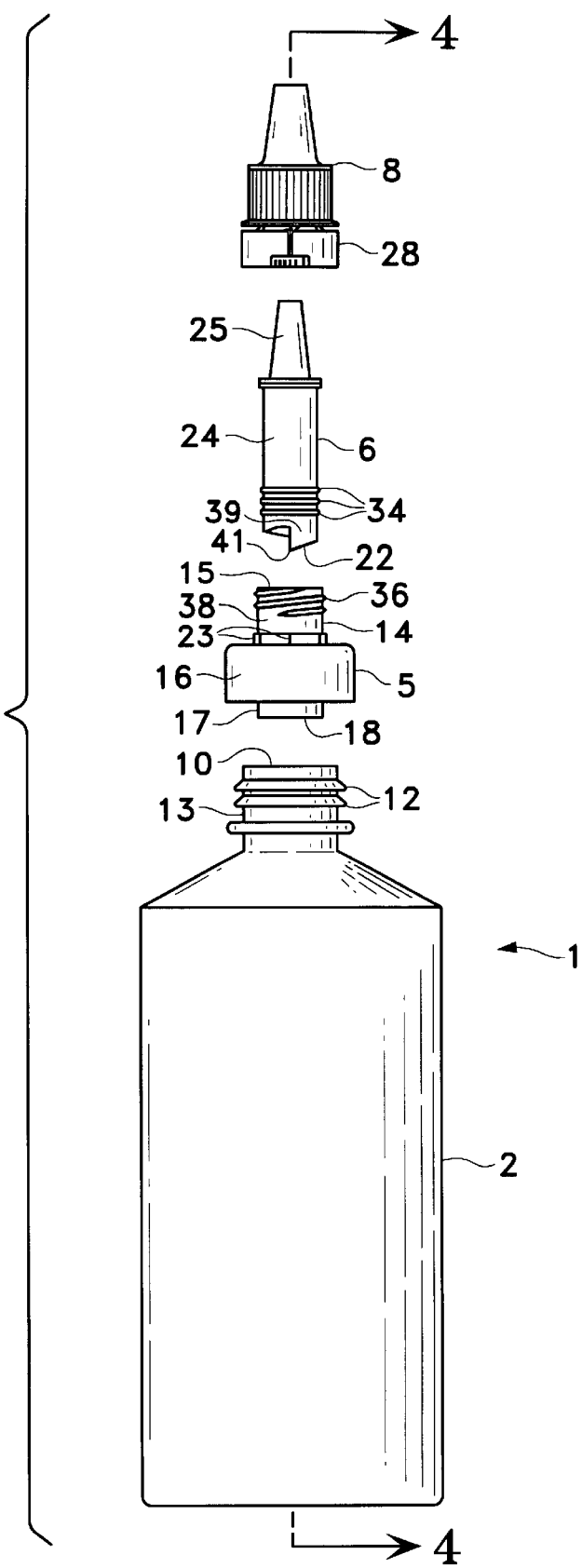
FIG. 3 is an exploded elevation view of a preferred embodiment of the invention.
Figure 4:
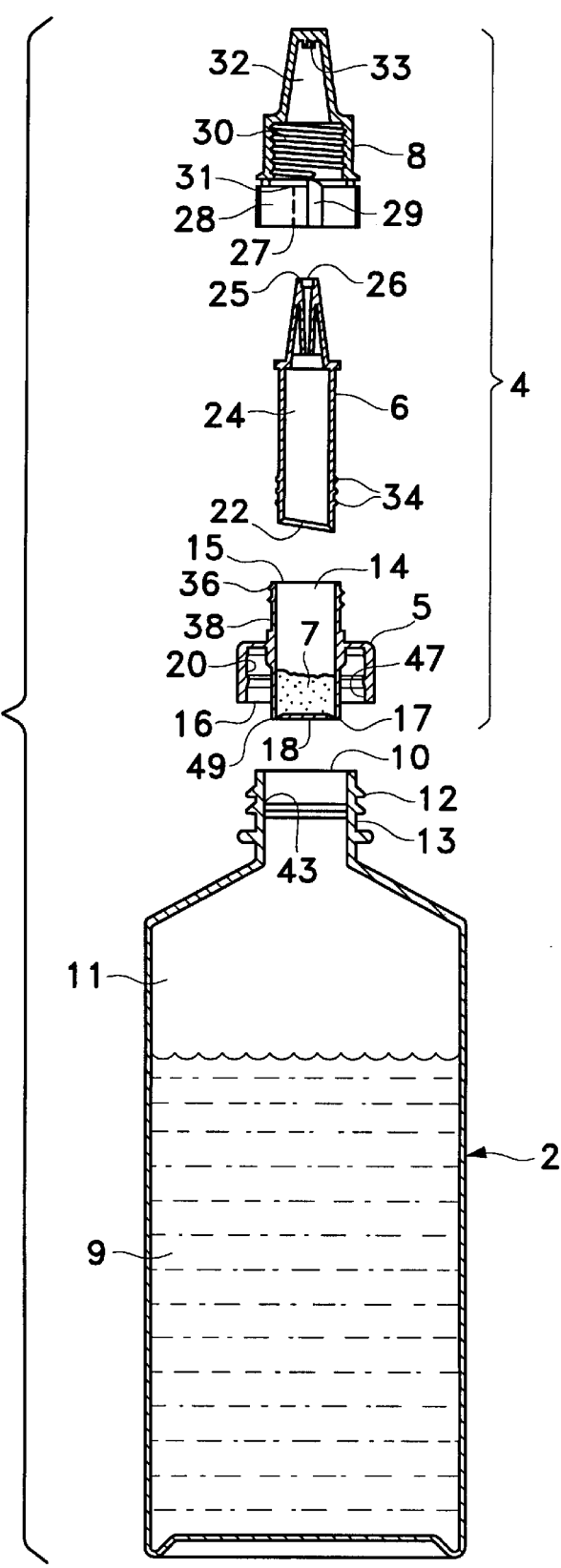
FIG. 4 is an exploded cross-section view of a preferred embodiment of the invention about line 4—4 of FIG. 3.

As illustrated in FIGS. 2–4; bottle 2 comprises neck 13, opening 10, external rings 12 and internal rings 43. Neck 13 is formed such that rings 12 annularly protrude from neck 13. Bottle 2 is made generally of molded polyethylene, although other materials such as polyethyleneterphlalate (PET) and polypropylene (P/P) may be used.

Figure 7:
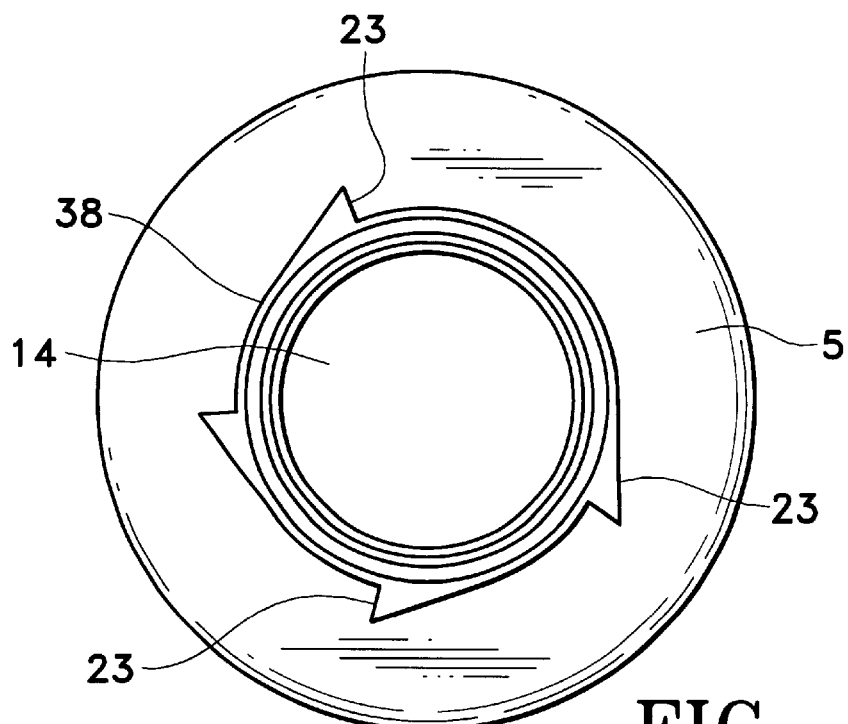
FIG. 7 is a top plan view of a housing of the invention.
Figure 8:
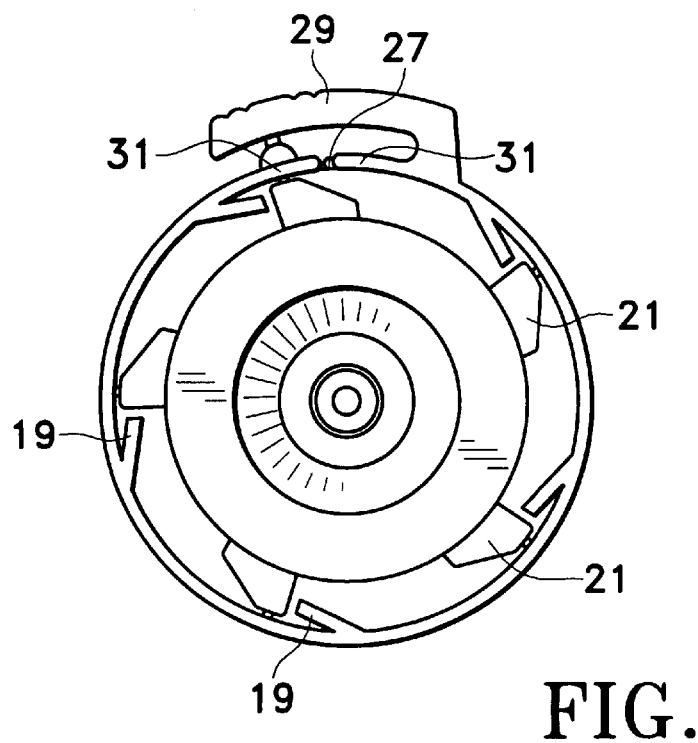
FIG. 8 is a bottom plan view of a cap and collar of the invention.
Figure 9:
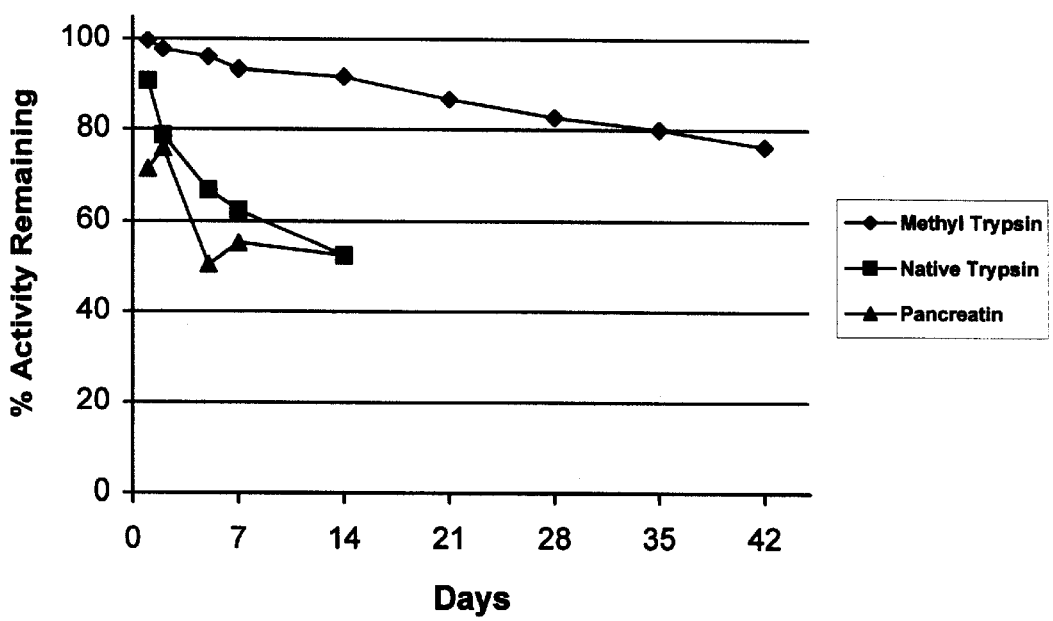
FIG. 9 is a graph comparing the proteolytic stability of methyl trypsin, trypsin and pancreatin in a multi-purpose composition, at 30° C. through 42 days.

As best seen in FIGS. 3 and 4, container 4 comprises housing 5, plunger 6, cap 8 and collar 28. Housing 5 comprises hollow cylinder 14 and cap 16. Cylinder 14 has external threads 36 annularly protruding near top end 15 and membrane disk 18 covering bottom end 17. Stops 23 are disposed annularly about exterior 38 of cylinder 14 (FIG. 7). Membrane 18 has thin cross-sectional thickness 49 about its circumference. Cap 16 has protruding internal rings 20, and cylinder 14 is coaxially disposed within cap 16 such that top end 15 and bottom end 17 project out of cap 16. Plunger 6 comprises hollow cylinder 24, open end 22, dispensing end 25 and ribs 34. Open end 22 has tooth 39 and is thinner in cross-sectional thickness than the thickness of hollow cylinder 24, thereby forming sharp point 41 of tooth 39. Cap 8 comprises pin 33, hollow cone 32, internal threads 30 and stops 21. As best seen in FIG. 8, collar 28 has tab 29, spokes 19 and perforation 27 which forms ends 31. Container 4 components are generally made of molded high density polyethylene or polycarbonate, but other materials and methods of manufacture such as P/P, PET, polystyrene and acrylonitrile butadiene styrene (ABS) may be employed.

Figure 5:
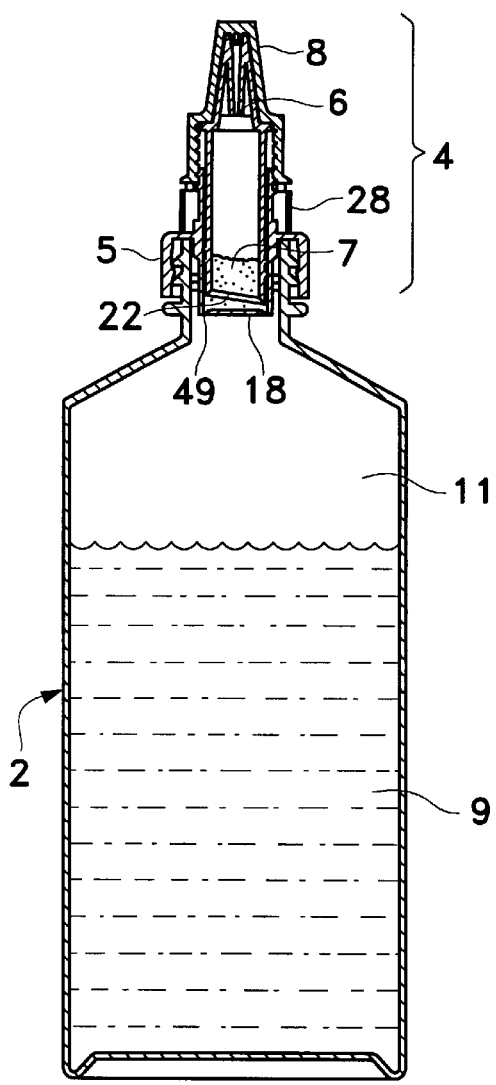
FIG. 5 is a cross-section view about line 5—5 of FIG. 2 of a preferred embodiment of the invention.
Figure 6:
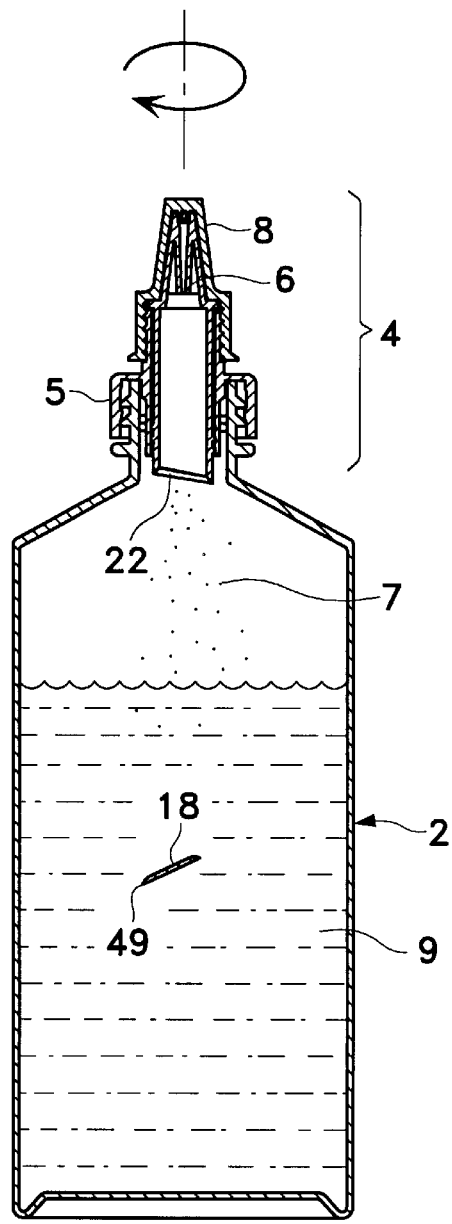
FIG. 6 is a cross-section view about line 5—5 of FIG. 2 of a preferred embodiment of the invention, illustrating the downward rotation of a cap/plunger assembly, the breaking of a membrane, and the egress of an enzyme composition.

As illustrated in FIG. 4, container 4 is put together by first adding Al-trypsin cleaning composition 7 to hollow cylinder 14 of housing 5, ringing collar 28 over cylinder 14, inserting plunger 6 within cylinder 14 such that rings 34 of plunger 6 compress against the interior of cylinder 14, and screwing on cap 8 over plunger 6, engaging pin 33 of cap 8 with notch 26 of plunger 6, by threading internal threads 30 within threads 36 of housing 5. In this configuration, spokes 19 of collar 28 are interspersed between both stops 21 of cap 8 and stops 23 of housing 5. Cap 8 in this configuration (see FIGS. 2 and 5), is only partially threaded within threads 36 of housing 5 due to the prevention of further downward rotation of cap 8 by collar 28. Aqueous composition 9 is added to bottle 2, container 4 is then placed over neck 13, and cap 16 is forced down on neck 13 such that rings 20 compress radially against neck 13, and exterior rings 12 compress against interior 47 of cap 16, forming an air-tight seal.

In operation, collar 28 is first removed from container 4 by screwing cap 8 downward on housing 5. When cap 8 is rotated, stops 21 engage and pull spokes 19, while stops 23 hold spokes 19 stationary. The resulting stress causes collar 28 to split at perforation 27. Split collar 28 may then be removed by pulling on tab 29. Cap 8 is then further screwed down on housing 5. With cap 8 rotation, plunger 6, is simultaneously pushed downward causing plunger 6 to descend cylinder 14. When plunger 6 reaches membrane 18 of housing 5, sharp point 41 punctures thin circumference 49 of membrane 18. Further rotation of cap 8 causes open end 22 of plunger 6 to further descend, slicing off membrane 18 about its circumference from housing 5, similar to the operation of a punch press. At this point the Al-trypsin cleaning composition contained in housing 5 is exposed to interior 11 of bottle 2 and falls into aqueous diluting composition 9 of bottle 2. Bottle 2 may then be inverted and shook, thus affecting the mixing of the Al-trypsin and aqueous diluting compositions. When membrane 18 is cut away from housing 5, a channel is formed which runs from bottle 2 through now open housing 5, plunger 6 and dispensing end 25. With the removal of cap 8, the resultant multi-purpose composition may now be dispensed through this channel to an appropriate container for cleaning, disinfecting, rinsing and storing the contact lens.

Other embodiments of two-compartment bottle assemblies may be employed in the present invention. For example, a blister pouch and piercing means may be utilized as the enzyme compartment and break-away membrane component, respectively, of a bottle assembly.

As stated above, the present invention two-part systems are comprised of two separate compositions, which are then combined before initial use. Part I comprises an Al-trypsin and Part II comprises an aqueous diluting solution. The resultant multi-purpose composition may contain various other agents, but must contain: 1) an anti-microbial agent, 2) an Al-trypsin, 3) a buffering agent, 4) a tonicity agent, and 5) water. The multi-purpose compositions of the present invention are intended to function as storing, rinsing, cleaning and disinfecting solutions. Therefore, the multi-purpose compositions will be physiologically compatible with the eye.

The Part I sterile enzyme composition of the present invention comprises an Al-trypsin and various carriers.

As used herein, "Al-trypsin" refers to a covalently modified trypsin wherein one or more of its lysine epsilon-amino groups has been mono-alkylated or di-alkylated to form the corresponding monoalkylamino or dialkylamino group. The alkyl group attached to the amine may be a primary or branched $C_{1-12}$ group. Preferred Al-trypsins of the present invention are those wherein the alkyl group is a primary or branched $C_{1-4}$ group. Alkylation of trypsin is generally performed by reductive alkylation. The degree of alkylation of the lysine epsilon-amino groups will depend on the reaction conditions of the reductive alkylation process. For example, if the reaction cycle is repeated a number of times and/or a higher reagent to enzyme ratio is used, then full alkylation, i.e., alkylation of all of the lysine epsilon-amino groups, will tend to be achieved. Al-trypsins of the present invention will preferably be fully dialkylyated at all of their lysine epsilon-amino groups. The most preferred Al-trypsin is methyl trypsin ("Me-trypsin"). The most preferred Me-trypsin of the present invention will be derived from porcine tissue sources and will be fully dimethylated, as described above.

Trypsin is a 23,800 dalton protease with 6 disulfide bridges. Trypsin can be synthesized or obtained from various sources, such as porcine, bovine or swine pancreatin. Trypsin is also available from commercial sources such as Sigma Chemical Co. (St. Louis, Mo.), Biofac Co. (United Kingdom) and Novo Nordisk (Denmark). Trypsin may vary from species to species, but in general will be highly homologous with porcine or human trypsin.

Al-trypsins may be synthesized by the process of reductive alkylation of trypsin, as generally described in Scheme 1, below.

Scheme 1

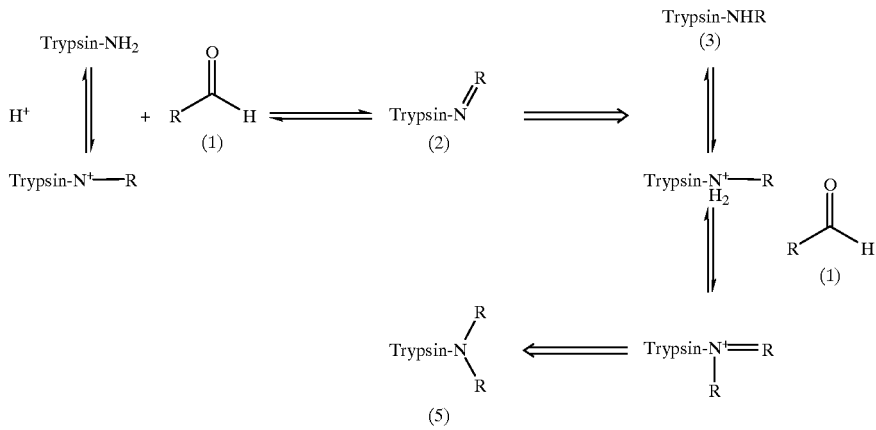

wherein, R is branched or unbranched $C_{1-12}$ alkyl.

As illustrated in scheme 1, the epsilon amino group of the lysine residues of trypsin is reacted with aldehydic alkylating reagent (1) to afford the alkylimino product (2). The alkylimino product (2) reduces to the resonant alkylamino species (3,4). The product (3,4) may react with another mole of the alkylating reagent (1) to yield the dialkylamino trypsin (5). As illustrated above, the resultant alkylated trypsin may either be mono or dialkylated at the lysine epsilon-amino groups.

EXAMPLE 1

Me-trypsin may be prepared by the following synthesis: The following solutions are first prepared:
1. Borate buffer: 0.2 M sodium borate buffer, pH 9.2 containing 2 mg/ml benzamidine hydrochloride and a trace amount of n-octanol.
2. Trypsin: 1 g in 150 ml borate buffer.

To the 150 ml solution of trypsin, 10 ml of 1 M sodium borohydride is added followed quickly by 10 ml of 2.4 M formaldehyde. Three more volumes of sodium borohydride and formaldehyde are added at 10 minute intervals. The reaction solution is then acidified with glacial acetic acid to approximately pH 4.2 and then dialyzed extensively against 2 mM HCl at 4° C. (8 changes of 2 L each within 24 hours). The dialyzed solution is finally lyophylized for over 20 hours.

The above reactions are further described in Rice, R H, Means, G E and Brown, W D. Stabilization of bovine trypsin by reductive methylation, *Biochimica et Biophysica Acta*, volume 492, pages 316–321 (1977); and Means, G E and Feeney, R E. Reductive alkylation of amino groups in proteins, *Biochemistry*, volume 7, pages 2192–2210 (1968). Me-trypsin is also available from commercial sources such as Sigma Chemical Co. and Promega Corp: (Madison, Wis.).

Other Al-trypsins may be prepared by methods analogous to Example 1, wherein formaldehyde is replaced by other alkylating reagents. For example, ethyl trypsin ("Et-trypsin") may be synthesized by an analogous method described in Example 1 and Scheme 1 above, wherein acetaldehyde is used as the alkylating reagent in place of formaldehyde.

As stated above, the Part I sterile enzyme composition of the present invention generally comprises an Al-trypsin and various carriers. The enzyme composition may be formulated as a powder, tablet or liquid. Dry powder or tablet compositions may be preferred when the Part I enzyme compositions need to be stable for longer periods of time than liquids. Excipients which make up the enzyme powder compositions are known in the art. Generally, the Al-trypsin composition will include bulking agents to carry the relatively small volume of an Al-trypsin into the diluting solution. Such bulking agents typically include polyols (e.g., mannitol or soribitol), polyethylene glycols (molecular weights greater than 1000) and sugars. Other excipients may include salts such as NaCl, chelating agents such as EDTA, and buffering agents such as Tris. Other additives may include surfactants to ease dispersion and dissolution of the powder in water. Preferred Al-trypsin compositions comprise mannitol and polyethylene glycol-5000 (PEG-5000).

Enzyme tablet compositions and methods of manufacturing are known in the art. Enzyme tablets require the use of bulking agents and binding agents. Additionally, tablets may contain effervescing agents such as bicarbonate to expedite dissolution of the tablet into the diluting solution. Other excipients known in the art may be added to provide greater consistency and easier manufacture of the tablets. Preferred Al-trypsin tablet compositions comprise sodium bicarbonate, citric acid, PEG-8000, carboxymethyl cellulose and lactose.

Liquid Al-trypsin compositions are preferred Part I compositions of the present invention due to their ease of preparation, sterilization and dispensing within the enzyme container of a bottle assembly. Liquid Al-trypsin compositions are solubilized in a suitable liquid vehicle. As used herein, "suitable liquid vehicle" refers to an aqueous or non-aqueous composition which, when diluted with an aqueous solvent described below, is compatible with the requirements of contact lens care regimens.

Non-aqueous Al-trypsin compositions employed as Part I compositions of the present invention generally comprise a crystalline enzyme uniformly dispersed in a water-soluble organic liquid. Typical organic liquids include polyoxyethylenes (e.g., PEG-400) and alkoxy polyoxyethylenes such as methoxy polyethylene glycols. In this composition, the Al-trypsin is in a dormant state, and following dissolution in a Part II composition of the present invention, the Al-trypsin solubilizes and becomes active. Preferred non-aqueous enzyme compositions comprise an enzyme in PEG-400.

Aqueous Al-trypsin compositions employed as Part I compositions of the present invention generally comprise a water-soluble organic liquid. It has been found that the use of a concentrated aqueous vehicle which contains a water-miscible organic molecule further enhances the stability of the Al-trypsin. The use of this type of vehicle is therefore preferred. As used herein, the term "water-miscible organic molecule" or "stabilizer," refers to an organic compound that forms one liquid phase with water when added to water. While not intending to be bound by any theory, it is believed that the stabilizers compete with water in the hydrogen bonding of the enzyme in solution, and thereby disrupt the active state of the enzymes. Therefore, the particular structure of the stabilizer is generally not an important factor to stabilization efficacy. It is rather the ability of the organic molecule to form one phase with water that determines its stabilizing utility in the present invention. Furthermore, the stabilizers must also be suitable for ophthalmic use and will thus exhibit minimal adverse effects in the cleaning or cleaning and disinfecting regimen. For example, the stabilizer will not contribute to ocular irritation/toxicity or interfere with the anti-microbial efficacy of an anti-microbial agent. Given the above criteria, various and numerous molecules may be used in the present invention to stabilize the Al-trypsin.

The stabilizers will be employed in the Part I liquid concentrates in an amount of from 10–90% weight/volume ("w/v"), and preferably, in an amount of from 40–80% (w/v). In general, the stabilizers will be polar, non-volatile, non-ionic or amphoteric molecules. Examples of stabilizers include polyols (polymers and monomers), and poorly metabolized sugars, including disaccharide or monomeric sugars. The above stabilizers are well known in the art and are available from numerous commercial sources. Examples of polymeric polyols are polyethylene glycol 200 (PEG 200) and PEG 400.

The preferred polyols utilized in the Part I concentrated aqueous compositions are 2–3 carbon polyols. As used herein, the term "2–3 carbon polyol" refers to a compound with 2 to 3 carbon atoms and at least two hydroxy groups. Examples of 2–3 carbon polyols are glycerol, 1,2-propane diol ("propylene glycol"), 1,3-propane diol and ethylene glycol. Propylene glycol is the preferred 2–3 carbon polyol.

Preferred Part I compositions of the present invention will also include an effective amount of a borate/boric acid compound. As used herein, "borate/boric acid compound" refers to an inorganic compound comprising boron and one or more oxygen groups, and which is either in acid or base form when dissolved in a composition of the present invention. Sources of borate/boric acid compounds include alkali metal salts of borate, boric acid and borax. As used herein, "effective amount of a borate/boric acid compound" refers to that amount of a borate/boric acid compound contained in a Part I Al-trypsin composition which enhances the proteolytic stability of an Al-trypsin. While such an amount will vary depending on other components present in the concentrate, the amount will be about 0.3 to 8.0% (w/v). Preferred amounts will be of from 0.5 to 1.5% (w/v). The borate/boric acid compound may also contribute to the anti-microbial preservation of the liquid enzyme compositions of the present invention to a level effective for multi-use dispensing. The solubility of the borates may be limited in water. The solubility of these compounds, however, may be increased by increasing the amount of polyol employed.

The preferred Part I compositions of the present invention will also contain an effective amount of calcium ion. The calcium ion contained in the compositions of the present invention may be obtained by the addition of various calcium salts. For example, the calcium ion source may be obtained from calcium chloride, calcium acetate and calcium ascorbate or other water soluble salts of calcium. The most preferred calcium ion source is calcium chloride. As used herein, "effective amount of calcium ion" refers to that amount of calcium ion which enhances the proteolytic stability of an Al-trypsin in the Part I compositions of the present invention. While that amount will vary depending upon the various components present, typical calcium ion concentrations will be about 1 to 90 millimolar. Preferred concentrations will be about 4.5 to 45 millimolar, and most preferred concentrations will be of from 10 to 25 millimolar.

The Part I compositions of the present invention may also include an acidic compound. Examples of acidic compounds include alkyl ($C_1$ to $C_6$) carboxylic acid compounds, such as formic, acetic and propionic acids, as well as other acids, such as aromatic carboxylic and aromatic sulfonic acids. The solubility of the acids may be limited in water. However, the solubility of these compounds may be increased by increasing the amount of polyol employed.

Other agents may also be employed in the Part I compositions of the present invention. For example, other divalent cations, such as magnesium, may also be employed. The compositions may additionally contain preservatives. Examples of suitable preservatives include sorbic acid and salts of sorbic acid, chlorhexidine, parabens as well as those compounds detailed below in the description of anti-microbial agents useful as disinfectants in the cleaning and disinfecting methods of the present invention. Still other agents may be added to the present invention including pH adjusting agents such as triethanolamine, Tris, HCl, or NaOH, and surfactants such as cationic, non-ionic, or amphoteric compounds.

Preferred Part I compositions containing a monomeric polyol, will contain an effective amount of an Al-trypsin, about 40–60% (w/v) of a 2–3 carbon polyol, 0.5–1.5% (w/v) of a borate/boric acid compound, 0.1–0.25% (w/v) calcium chloride and water. The most preferred composition of this type will contain an effective amount of an Al-trypsin, 50% (w/v) propylene glycol, 1.5% (w/v) of a borate/boric acid compound, 0.25% (w/v) calcium chloride and water.

Preferred Part I compositions containing a polymeric polyol will contain an amount of an Al-trypsin, about 15–25% (w/v) of a 2–3 carbon polyol, 25–50% (w/v) of a polymeric polyol, 0.5–2.0% (w/v) of a borate/boric acid compound, 0.1–0.25% (w/v) calcium chloride and water. The most preferred composition of this type will contain an effective amount of an Al-trypsin, 25% (w/v) glycerol, 50% (w/v) PEG-400, 1.5% (w/v) of a borate/boric acid compound, 0.25% (w/v) calcium chloride and water.

As stated above, the anti-microbial agent(s) of the present invention may be included in any of the Al-trypsin compositions described herein. The actual amount of anti-microbial agent will vary, but will provide effective disinfection of the contact lens, as described below.

The above-described Part I Al-trypsin compositions are aseptically processed generally by sterile filtering the liquids, or lyophilization, aseptic processing and terminal gamma irradiation of the solids. These and other methods of sterilizing liquids or solid compositions are well known in the art.

The Part I Al-trypsin concentration will depend on various factors, such as: the particular Al-trypsin, combination of Al-trypsins and purity of the Al-trypsin(s) selected, the quantity of Al-trypsin composition to be added to the Part II aqueous composition; the volume of the Part II aqueous composition; the type of lenses to be cleaned; and the intended duration of each cleaning. For example, if an Al-trypsin containing one or only a few lysine alkylations (which is inherently less stable than more fully alkylated trypsins) is chosen, the concentration of that enzyme in a Part I composition may need to be increased.

During storage, some of the activity of the Al-trypsin may be lost, depending on length of storage and temperature conditions. Thus, the Part I enzyme compositions of the present invention may be prepared with initial amounts of the Al-trypsin that exceed the amount necessary to achieve the final multi-purpose enzyme concentration ranges described herein. In general, the Part I Al-trypsin compositions of the present invention will preferably contain an Al-trypsin in an amount of from about 100–100,000 PAU/g or 100–100,000 PAU/mL.

The Part I Al-trypsin compositions, however, will contain an amount of an Al-trypsin sufficient to remove substantially or reduce significantly deposits of proteins, lipids, Hi mucopolysaccharides and other materials typically found on human-worn contact lenses when a relatively small amount of a Part I Al-trypsin composition is mixed with a Part II aqueous diluting composition. As used herein, such a final Al-trypsin concentration of the resultant multi-purpose composition of the present invention is referred to as "an amount effective to clean the lens." However, the cleaning methods of the present invention will generally employ an amount of the above-described Al-trypsin compositions sufficient to provide a final Al-trypsin concentration in the multi-purpose composition of from about 1–100 PAU/mL of solution, following dispersion of a Part I Al-trypsin composition in a Part II composition. A final concentration of about 5–25 PAU/mL is preferred. For purposes of this specification, a "proteolytic activity unit" or "PAU" is defined as the amount of enzyme activity necessary to generate one microgram (mcg) of tyrosine per minute ("mcg Tyr/min"), as determined by the casein-digestion, colorimetric assay described below.

Casein-Digestion Assay

A 5.0 mL portion of casein substrate (0.65% casein w/v) is equilibrated for 10 minutes (min) ±5 seconds (sec) at 37° C. An enzyme solution is prepared from a Part I enzyme composition by solubilizing and diluting the Part I composition in PBS buffer. A 1.0 mL portion of this enzyme solution (0.2 mg/ml) is then added to the casein substrate and the mixture vortexed, then incubated for 10 min ±5 sec at 37° C. After incubation, 5.0 mL of 14% trichloroacetic acid is added and the resultant mixture immediately vortexed. The mixture is incubated for at least another 30 min, then vortexed and centrifuged for 15–20 min (approx. 2000 rpm). The supernatant of the centrifuged sample is filtered into a serum filter sampler and a 2.0 mL aliquot removed. To the 2.0 mL sample is added 5.0 mL of 5.3% $Na_2CO_3$. The sample is vortexed, 1.0 mL of 0.67 N Folin's Phenol reagent is added, and the is sample is immediately vortexed again, then incubated for 60 min at 37° C. The sample is then read on a visible light spectrophotometer at 660 nanometers (nm) versus purified water as the reference. The sample concentration is then determined by comparison to a tyrosine standard curve. The Part I concentration is then calculated by taking into account the dilution ratio.

The Part II aqueous compositions provide the volume of distilled water necessary for the multi-purpose compositions of the present invention. In general, the Part II composition may also contain sodium chloride and other excipients which together provide an ophthalmically compatible solution. However, as noted above, Part I compositions may contain a percentage or all of these ingredients, and Part II compositions may provide only a percentage of these ingredients, or none at all. As will be appreciated by those skilled in the art, the Part II compositions utilized in the present invention may contain various other components such as suitable buffering agents, chelating and/or sequestering agents and tonicity adjusting agents. The Part II compositions may also contain surfactants. As stated above, the anti-microbial agent may also be included in the Part II compositions. In general, the Part II compositions will contain one or more anti-microbial agents (e.g., PHMB or polyquaternium-1), a buffer (e.g., borate), citrates, tonicity agents (e.g., NaCl, sugars), a chelating agent (e.g., EDTA), and surfactants (e.g., block copolymers). Other agents which enhance the anti-microbial efficacy of the compositions, such as amino alcohols and alkylamines, may also be added. Preferred Part II compositions comprise polyquaternium-1, sodium borate, boric acid, propylene glycol and Pluronic P-103. The most preferred Part II compositions comprise boric acid, sorbitol, 95% 2-amino-2-methyl-1-propanol ("AMP-95"), sodium citrate, sodium chloride, disodium edetate, polyquaternium-1, poloxamer 1304 ("Tetronic 1304") and myristamidopropyl diamethyl amine ("MAPDA").

The multi-purpose compositions are intended to be used with various types of contact lenses including rigid gas-permeable ("RGP") lenses and soft lenses.

The cleaning obtained with the liquid enzyme compositions of the present invention is a function of the time. The soaking times utilized will generally vary from about 1 hour to overnight. However, if longer soaking periods (e.g., 24 hours) were to be employed, lower concentrations than those described above may be utilized.

The cleaning and disinfecting methods of the present invention involve the use of a small volume of the above-described Part I Al-trypsin compositions to facilitate the removal of proteins and other deposits from contact lenses. The volume of enzyme composition used in particular embodiments of the present invention may vary, depending on the Al-trypsin concentration, as described above, as well as various other factors, such as the purity of the Al-trypsin, the proposed duration of exposure of lenses to the compositions, the nature of the lens care regimen (e.g., the frequency of lens disinfection and cleaning), the type of lens being treated, and the use of adjunctive cleaning agents (e.g., surfactants). In general, about 1 gram of powder, 1 tablet or 1 milliliter of a Part I Al-trypsin composition will be added to about 120 mL of a Part II composition, although greater or lesser amounts are contemplated by the present invention.

The Part I Al-trypsin compositions of the present invention will demonstrate effective cleaning efficacy while exhibiting minimal adverse effects or, more preferably, enhanced effects on the anti-microbial activity of anti-microbial agents. The anti-microbial activity of disinfecting agents, particularly polymeric quaternary ammonium compounds such as polyquaternium-1, is adversely affected by high concentrations of sodium chloride or other ionic solutes. More specifically, polymeric quaternary ammonium compounds, and particularly those of Formula (I), below, lose anti-microbial activity when the concentration of ionic solutes in the multi-purpose compositions is too high. Generally, the multi-purpose compositions of the present invention will have tonicities/osmolalities in the range of hypotonic to isotonic, and more preferably in the range of 150 to 350 milliOsmoles per kilogram (mOs/kg). A range of 200 to 300 mOs/kg is particularly preferred, and an osmolality of about 270 mOs/kg is most preferred.

The cleaning and disinfecting methods of the present invention utilize a multi-purpose composition of the present invention containing an anti-microbial agent Anti-microbial agents will generally be non-oxidative polymeric anti-microbial agents which derive their anti-microbial activity through a chemical or physicochemical interaction with the organisms. As used in the present specification, the term "polymeric anti-microbial agent" refers to any nitrogen-containing polymer or co-polymer which has anti-microbial activity. Preferred polymeric anti-microbial agents include: polyquaternium-1, which is a polymeric quaternary ammonium compound; and polyhexamethylene biguanide ("PHMB") or polyaminopropyl biguanide ("PAPB"), which are polymeric biguanides. These preferred anti-microbial agents are disclosed in U.S. Pat. Nos. 4,407,791 and 4,525,346, issued to Stark, and 4,758,595 and 4,836,986, issued to Ogunbiyi, respectively. The entire contents of the foregoing publications are hereby incorporated in the present specification by reference. Other anti-microbial agents suitable in the methods of the present invention include: other quaternary ammonium compounds, such as benzalkonium halides, and other biguanides, such as chlorhexidine. The anti-microbial agents used herein are preferably employed in the absence of mercury-containing compounds such as thimerosal.

The most preferred anti-microbial agents are polymeric quaternary ammonium compounds of the structure:

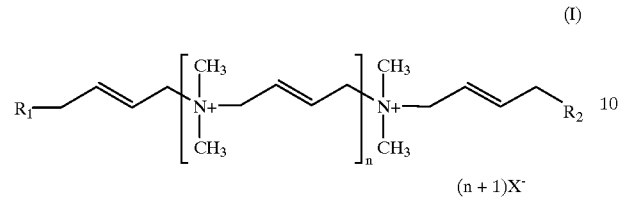

(I)

wherein:
R$_1$ and R$_2$ can be the same or different and are selected from:
N$^+$(CH$_2$CH$_2$OH)$_3$X$^-$;
N(CH$_3$)$_2$ or OH;
X$^-$ is a pharmaceutically acceptable anion, preferably chloride; and
n=integer from 1 to 50.

The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein X$^-$ is chloride and R$_1$, R$_2$ and n are as defined above.

The above-described anti-microbial agents are utilized in the methods of the present invention in an amount effective to eliminate substantially or to reduce significantly the number of viable microorganisms found on contact lenses, in accordance with the requirements of governmental regulatory agencies, such as the United States Food and Drug administration. For purposes of the present specification, that amount is referred to as being "an amount effective to disinfect" or "an anti-microbially effective amount." The amount of anti-microbial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of anti-microbial agent required to disinfect the lenses. The type of lens being treated (e.g., "hard" versus "soft" lenses) may also be a factor. In general, a concentration in the range of about 0.00001% to about 0.01% by weight of one or more of the above-described anti-microbial agents will be employed. The most preferred concentration of the polymeric quaternary ammonium compounds of Formula (I) is about 0.001% by weight.

The methods of the present invention will typically involve adding about 2–10 mL of a multi-purpose composition of the present invention to a lens case, placing the soiled lens into the dispensed multi-purpose composition, and soaking the lens for a period of time effective to clean and disinfect the lens. Optionally, the contact lenses are first rubbed with a multi-purpose composition of the present invention or a surfactant cleaner prior to immersion in the multi-purpose composition. The lens will typically be soaked overnight, but shorter or longer durations are contemplated by the methods of the present invention. A soaking time of 4 to 8 hours is preferred. The methods of the present invention allow the above-described regimen to be performed daily.

The following examples are presented to illustrate further, various aspects of the present invention, but are not intended to limit the scope of the invention in any respect.

EXAMPLE 2

A preferred Part I Me-trypsin composition and a preferred Part II aqueous composition containing an anti-microbial agent for use in a two-component bottle assembly/multi-purpose composition of the present invention, are described below:

| A. Part I Me-Trypsin Composition | |
| --- | --- |
| Ingredient | Amount |
| Me-Trypsin | 3000 PAU/mL |
| Boric acid | 1.5% (w/v) |
| Propylene glycol | 50% (w/v) |
| Calcium chloride | 0.25% (w/v) |
| NaOH/HCl | QS to adjust pH to 6 to 8 |
| Purified water | QS |

Calcium chloride and boric acid are dispersed in 30% of the volume of purified water. Propylene glycol is then added. The pH of the solution is adjusted, and Me-trypsin is then dissolved in the solution, followed by a final volume adjustment with purified water. The composition is then sterile filtered using a 0.2 μm filter.

| B. Part II Aqueous Composition | |
| --- | --- |
| Ingredient | % (w/v) |
| Polyquaternium-1 | 0.001 |
| Boric acid | 0.6 |
| Sodium chloride | 0.1 |
| AMP-95 | 0.45 |
| MAPDA | 0.0005 |
| Sorbitol | 1.2 |
| Sodium citrate | 0.65 |
| Tetronic 1304 | 0.05 |
| Disodium Edetate | 0.05 |
| NaOH/HCl | To adjust pH 6.5 to 8.0 |
| Purified water | QS |

The ingredients are dissolved with 90% of the volume of purified water, the pH is adjusted, and the volume is then brought up to 100% volume. The composition is then sterile filtered using a 0.2 μm membrane filter.

Various volumes of the above Part I enzyme and Part II aqueous compositions may be employed in a two-compartment bottle assembly of the present invention. Preferred amounts include 1 mL of the enzyme composition and 120 mL of the aqueous composition.

EXAMPLE 3

The following are examples of Part I Me-trypsin compositions of the present invention:

| A. Part I composition: | |
| --- | --- |
| Ingredient | Amount |
| Me-trypsin | 2200 PAU/mL |
| Sodium borate | 1.5% (w/v) |
| Glycerol | 25% (w/v) |
| PEG-400 | 50% (w/v) |
| POLYQUAD ® | 0.003% (w/v) |
| NaOH/HCl | QS to pH 5 to 8 |

-continued

A. Part I composition:

| Ingredient | Amount |
|---|---|
| Calcium chloride | 0.25% (w/v) |
| Water | QS |

The above formulation is prepared by first sequentially mixing glycerol, PEG-400, POLYQUAD®, purified water, hydrochloric acid and sodium borate together. The required amount of Me-trypsin (about 0.3 w/v) is then dissolved the above mixture, the pH is adjusted and the solution is brought to 100% volume. The enzyme composition is then sterile filtered (0.2 μm filter). The optimal pH of the above formulation will be in the range of 6–7; a pH of 6.5 is most preferred.

B. Part I composition:

| Ingredient | Amount |
|---|---|
| Me-Trypsin | 2200 PAU/mL |
| Sodium borate | 7.62% (w/v) |
| Propylene glycol | 50% (v/v) |
| Water | QS |
| NaOH/HCl | QS to pH 6.0 |

The above composition is prepared by methods analogous to those disclosed in Example 3A.

C. Part I Et-trypsin composition:

| Ingredient | Amount |
|---|---|
| Et-Trypsin | 3000 PAU/mL |
| Boric acid | 1.5% (w/v) |
| Propylene glycol | 50% (w/v) |
| Calcium chloride | 0.25% (w/v) |
| NaOH/HCl | QS to adjust pH to 6 to 8 |
| Purified water | QS |

The above composition may be prepared by methods analogous to those described in Example 3A.

EXAMPLE 4

The following are examples of preferred Part I solid Me-trypsin compositions of the present invention.

A. Part I Al-Trypsin Tablet Composition

| Ingredient | Amount |
|---|---|
| Al-Trypsin | 4000 PAU |
| Sodium bicarbonate | 8.5 mg |
| Citric acid | 3.5 mg |
| PEG-3350 | 3.0 mg |
| Lactose | QS to 50 mg |

The tablets are generally prepared by first mixing the appropriate amounts of each of the ingredients and then passing the mixture through an oscillating granulator equipped with a 20 mesh hard screen. The screened ingredients are then added to a suitably sized blender and mixed for 30 minutes. An appropriate amount of PEG and Me-trypsin are then passed through a 20 mesh hard screen and this mixture is then added to the blender. The combined screened ingredients are then blended for an additional 15 minutes. Using a tablet press equipped with a 5/32" tooling, the blended ingredients are then compressed into tablets having a target weight of 50–80 mg and a hardness of 8 SCU. The tablets may then be sterilized by the method of gamma-sterilization.

B. Part I Me-Trypsin Powder Composition

| Ingredient | Amount |
|---|---|
| Me-trypsin | 3000 PAU (~3–4 mg) |
| Lactose | QS to 1 g |

The enzyme and lactose are dissolved in water (1 g of enzyme/lactose per 1 mL of water) and sterile filtered using a 0.2 μm filter. The sterile enzyme solution as then aseptically lyophilized.

EXAMPLE 5

The following are examples of Part II disinfecting compositions of the present invention:

| Ingredient | Amount % (w/v) |
|---|---|
| A. Part II Disinfecting Composition | |
| Polyquaternium-1 | 0.0002 |
| Sodium borate | 0.25 |
| Propylene glycol | 1.0 |
| Pluronic P-103 | 0.1 |
| NaOH/HCl | To adjust pH to 6.5 to 8.0 |
| Purified water | QS |
| B. Part II Disinfecting Composition: | |
| PHMB | 0.0001 |
| Sodium phosphate | 0.28 |
| Potassium phosphate | 0.06 |
| Sodium chloride | 0.7 |
| Disodium edetate | 0.0% |
| NaOH/HCl | To adjust to pH 6.5 to 8.0 |
| Purified water | QS |
| C. Part II Disinfecting Composition: | |
| Polyquaternium-1 | 0.001% + 10% excess |
| Sodium chloride | 0.48 |
| Disodium Edetate | 0.05 |
| Citric acid monohydrate | 0.021 |
| Sodium citrate dihydrate | 0.56 |
| NaOH/HCl | To adjust to pH 6.5 to 8.0 |
| Purified water | QS |
| D. Part II Disinfecting Composition: | |
| Polyquaternium-1 | 0.001% + 10% excess |
| Sodium chloride | 0.48 |
| Boric Acid | 0.225 |
| Sodium Borate | 0.08 |
| Mannitol | 0.64 |
| Pationic 138C | 0.005 |
| Tetronic 1304 | 0.25 |
| Disodium Edetate | 0.05 |
| Citric acid monohydrate | 0.016 |
| Sodium citrate dihydrate | 0.46 |
| NaOH/HCl | To adjust to pH 6.5 to 8.0 |
| Purified water | QS |

These Part II compositions are prepared in a similar way as those of Example 2B.

The Part I and II compositions described in the Examples above will be combined, stored and mixed in a single bottle assembly in various quantities. In general, preferred amounts will be:

Part I: 1 g of powder or 1 tablet of a solid enzyme composition, or 1 ml of liquid enzyme composition.

Part II: about 120 ml (Similarly 2 g of powder, 2 tablets or 2 ml of liquid may be combined with about 240 ml of Part II.)

The preferred enzyme activity in the final multi-purpose solution will be about 5–25 PAU/ml.

EXAMPLE 6

A preferred multi-purpose composition of the present invention comprises:

| Ingredient | Amount % (w/v) |
| --- | --- |
| Me-trypsin | 25 PAU/mL |
| Sodium borate | 0.012 |
| Calcium Chloride | 0.002 |
| Propylene glycol | 0.41 |
| Polyquaternium-1 | 0.001 |
| Boric acid | 0.6 |
| Sodium chloride | 0.1 |
| AMP-95 | 0.45 |
| MAPDA | 0.0005 |
| Sorbitol | 1.2 |
| Sodium citrate | 0.65 |
| Tetronic 1304 | 0.05 |
| Disodium Edetate | 0.05 |
| NaOH/HCl | To adjust pH 6.5 to 8.0 |
| Purified water | QS |

The composition is prepared by adding 1 mL of the composition of Example 2A to 120 mL of Example 2B.

The enzyme stability examples below (Examples 7–11) employed the following enzyme assay:

Azocasemn Method:

The following solutions are used in this assay:

1) Buffer solution: 0.05 M sodium phosphate buffer containing 0.9% sodium chloride, pH 7.6.
2) Substrate solution: 2 mg/ml azocasein in the buffer solution mentioned above.

The assay is initiated by mixing 1 ml of an appropriately diluted (such that the enzyme activity is in the range of standard curve) enzyme composition in phosphate buffer with 2 ml of azocasein substrate solution (2 mg/ml). After incubation at 37° C. for 20 minutes, the mixture is removed from the incubator and 1 ml of trichloroacetic acid (14% w/v) is added to stop the enzyme reaction. The mixture is vortexed well and allowed to stand at room temperature for 20 minutes. After centrifuging at 2500 rpm (with a Beckman GS-6R Centrifuge) for 15 minutes, the supernatant is filtered with a serum sampler. 2 ml of the clear yellow filtrate is then adjusted to a neutral pH with 2 ml of 0.5 N sodium hydroxide and the absorbance of 440 nm wavelength light is measured with a spectrophotometer. The amount of azocasein hydrolyzed is calculated based on a standard curve of known concentrations of azocasein solution developed under identical conditions. An enzyme activity unit ("AZ U") is defined as that amount of enzyme which hydrolyzes 1 μg of azocasein substrate/minute at 37° C.

EXAMPLE 7

Data demonstrating the superior efficacy of Part I Me-trypsin compositions over analogous compositions containing either trypsin or acetylated trypsin, were ascertained. The enzymes were solubilized in a Part I composition containing 50% (w/v) L-sorbose 1% (w/v) borax ($Na_2B_4O_7 \cdot 10H_2O$), at pH 5.79, except the acetylated trypsin composition was at pH 7.54. The compositions were stored at 45° C. for 240 hours. At various time points, enzyme activity was assayed using the azocasein method. The data are illustrated in Table 1, below:

TABLE 1

Comparison of the Stability of Me-Trypsin Versus Other Trypsin Analogs

| | % Activity Remaining | | | | | |
| --- | --- | --- | --- | --- | --- | --- |
| Enzyme | 0 Hr. | 64 Hr. | 96 Hr. | 120 Hr. | 144 Hr. | 240 Hr. |
| Native Trypsin | 100.0 | 62.9 | 56.8 | 53.1 | 49.1 | 41.4 |
| Acetylated Trypsin | 100.0 | 53.1 | 45.1 | 42.2 | 38.5 | 31.0 |
| Methyl-Trypsin | 100.0 | 89.4 | 86.3 | 84.7 | 82.2 | 76.1 |

The data show the superior enzyme stability of Me-trypsin in a Part I composition of the present invention over other trypsin related enzyme compositions.

EXAMPLE 8

The following is an example of the proteolytic stability of a multi-purpose composition containing Me-trypsin as compared to analogous compositions containing trypsin or pancreatin. The enzymes were solubilized in the Example 5C composition. The compositions were stored at room temperature or 30° C. for up to 42 days. At various time points, enzyme activity was assayed using the azocasein method. The data are illustrated in Table 2, below:

TABLE 2

Comparison of the Stability of Me-Trypsin, Trypsin and Pancreatin in a Multi-purpose Composition

| | % Activity Remaining | | | | | | | | |
| --- | --- | --- | --- | --- | --- | --- | --- | --- | --- |
| Enzyme | 1 day | 2 days | 5 days | 7 days | 14 days | 21 days | 28 days | 35 days | 42 days |
| | RT | | | | | | | | |
| Methyl Trypsin | 100.9 | 100.8 | 97.9 | 99.4 | 100.0 | 98.5 | 96.6 | 96.5 | 94.0 |
| Native Trypsin | 102.5 | 101.5 | 98.5 | 93.6 | 85.7 | 79.6 | 74.4 | 73.8 | 61.3 |
| Pancreatin | 97.6 | 93.5 | 73.8 | 79.9 | 71.0 30° C. | 64.3 | 59.0 | — | — |

TABLE 2-continued

Comparison of the Stability of Me-Trypsin, Trypsin and Pancreatin in a Multi-purpose Composition

| Enzyme | % Activity Remaining | | | | | | | |
|---|---|---|---|---|---|---|---|---|
| | 1 day | 2 days | 5 days | 7 days | 14 days | 21 days | 28 days | 35 days | 42 days |
| Methyl Trypsin | 99.7 | 97.8 | 96.1 | 93.5 | 91.8 | 86.7 | 82.7 | 80.0 | 76.3 |
| Native Trypsin | 90.8 | 78.7 | 66.7 | 62.4 | 52.4 | — | — | — | — |
| Pancreatin | 71.4 | 75.9 | 50.5 | 55.2 | 52.5 | — | — | — | — |

* Enzyme concentration: 50 μg/ml for all the enzymes except pancreatin, which was 375 μg/ml.

The data presented in Table 2 demonstrate the superior stability of Me-trypsin in a disinfecting composition of the present invention over analogous compositions containing trypsin or pancreatin.

EXAMPLE 9

The following is an example of the proteolytic stability of a multi-purpose composition containing Me-trypsin as compared to analogous compositions containing trypsin. The enzymes were solubilized in the Example 5C composition. The two compositions were incubated at 35° C. or 40° C. At the appointed time, aliquots were tested for enzyme activity by the azocasein method. Activity levels were compared with initial levels and expressed as percent remaining activity. The results are presented in Table 3, below:

TABLE 3

Comparison of the Thermal Stability of Me-Trypsin and Trypsin in a Disinfecting Solution

| | % Activity Remaining | | | | | | |
|---|---|---|---|---|---|---|---|
| | 35° C. | | | | 40° C. | | |
| Enzymes* | 24 hrs | 48 hrs | 72 hrs | 168 hrs | 24 hrs | 114 hrs | 168 hrs |
| Native Trypsin | 69.9 | 55.9 | 48.5 | 37.6 | 42.4 | 19.4 | 17.4 |
| Methylated Trypsin | 97.6 | 96.4 | 91.6 | 87.3 | 88.9 | 75.2 | 67.0 |

* Enzyme concentration: 50 μg/ml

EXAMPLE 10

Data demonstrating the stability of the Part I Me-trypsin composition of Example 2A, at storage temperatures of room temperature, 40°, 45°, 50° and 55° C. were ascertained. At the appointed time, aliquots were tested for enzyme activity by the azocasein method. Activity levels were compared with initial levels and expressed as percent remaining activity. The results are presented in Table 4, below:

TABLE 4

Stability of Me-Trypsin in the Example 2A Composition

| Temperature | Storage Time (weeks) | Percent Remaining Activity |
|---|---|---|
| 55° C. | 1 | 82.1 |
| | 2 | 75.3 |
| | 4 | 46.5 |

TABLE 4-continued

Stability of Me-Trypsin in the Example 2A Composition

| Temperature | Storage Time (weeks) | Percent Remaining Activity |
|---|---|---|
| 50° C. | 1 | 91.8 |
| | 2 | 91.8 |
| | 4 | 82.4 |
| | 6 | 81.3 |
| | 8 | 75.2 |
| | 12 | 71.5 |
| 45° C. | 1 | 100 |
| | 2 | 100 |
| | 4 | 92.7 |
| | 6 | 97.8 |
| | 8 | 100 |
| | 12 | 97.6 |
| 40° C. | 1 | 100 |
| | 2 | 100 |
| | 4 | 93.7 |
| | 6 | 100 |
| | 8 | 100 |
| | 12 | 100 |
| RT | 1 | 100 |
| | 2 | 100 |
| | 4 | 94.1 |
| | 6 | 100 |
| | 8 | 100 |
| | 12 | 100 |

EXAMPLE 11

Data demonstrating the stability of the Me-trypsin multi-purpose composition of Example 6 (1 mL of Example 2A dispersed in 120 mL of Example 2B), in comparison to compositions containing either trypsin or pancreatin, were ascertained. The trypsin or pancreatin compositions were prepared by dispersing 1.4 mL of Example 3B (wherein Me-trypsin was replaced by either trypsin or pancreatin) in 120 mL of Example 2B. The compositions were incubated at room temperature, 30° and 35° C. At the appointed time, aliquots were tested for enzyme activity by the azocasein method. Activity levels were compared with initial levels and expressed as percent remaining activity. The results are presented in Table 5, below:

TABLE 5

Comparison of the Enzyme Stability of the Example 6 Composition With Other Compositions

| Temperature | Storage Time (weeks) | % Remaining Activity | | |
|---|---|---|---|---|
| | | Me-Trypsin | Trypsin | Pancreatin |
| 35° C. | 1 | 82.1 | 30.8 | 36.1 |
| | 2 | 75.0 | 19.9 | 39.6 |
| | 3 | 71.4 | 13.3 | 30.0 |

TABLE 5-continued

Comparison of the Enzyme Stability of the Example 6 Composition With Other Compositions

| Temperature | Storage Time (weeks) | % Remaining Activity | | |
|---|---|---|---|---|
| | | Me-Trypsin | Trypsin | Pancreatin |
| | 4 | 65.2 | 12.8 | 29.8 |
| | 6 | 55.9 | 8.8 | 27.5 |
| | 8 | 50.3 | 5.2 | 25.1 |
| 30° C. | 1 | 97.0 | 65.7 | 59.3 |
| | 2 | 97.2 | 54.6 | 59.9 |
| | 3 | 91.1 | 47.1 | 46.4 |
| | 4 | 90.6 | 44.9 | 51.6 |
| | 6 | 85.8 | 35.8 | 38.4 |
| | 8 | 83.0 | 30.4 | 35.5 |
| RT | 1 | 101.3 | 93.5 | 87.8 |
| | 2 | 99.6 | 86.8 | 85.3 |
| | 3 | 98.4 | 82.5 | 75.5 |
| | 4 | 98.1 | 79.5 | 81.0 |
| | 6 | 96.0 | 71.0 | 61.5 |
| | 8 | 96.4 | 64.2 | 56.0 |

EXAMPLE 12

The following is an example of the stability of Me-trypsin or Me-trypsin in a multi-purpose composition of the present invention as compared to an analogous composition containing trypsin. The enzymes were solubilized in the Example 2B composition. The compositions were stored at 37° or 50° C. for 8 days or 30 hours, respectively. At various time points, enzyme activity was assayed using the azocasein method. The data are illustrated in Tables 6 and 7, below:

TABLE 6

Comparison of the Stability of Et-Trypsin and Trypsin in a Multi-purpose Composition 37° C.
% Activity Remaining

| Enzyme | 1 Hour | 2 Hours | 4 Hours | 6 Hours | 8 Hours | 1 day | 2 days | 4 days | 8 days |
|---|---|---|---|---|---|---|---|---|---|
| Trypsin | 86.8 | 80.0 | 72.7 | 62.9 | 56.6 | 37.6 | 26.8 | 17.9 | 112 |
| Et-Trypsin | 100 | 100 | 95.2 | 99.3 | 97.9 | 89.7 | 82.5 | 76.4 | 65.6 |

* Enzyme concentration: 50 μg/ml for all the enzymes except pancreatin, which was 375 μg/ml.

TABLE 7

Comparison of the Stability of Et-Trypsin, Me-Trypsin and Trypsin in a Multi-purpose Composition 50° C.
% Activity Remaining

| Enzyme | 0.5 Hour | 1 Hour | 2 Hours | 4 Hours | 6 Hours | 22 Hours | 30 Hours |
|---|---|---|---|---|---|---|---|
| Trypsin | 81.1 | 66.2 | 45.9 | 31.8 | 19.4 | 9.3 | 4.5 |
| Me-Trypsin | 97.7 | 100 | 90.0 | 76.9 | 68.0 | 45.0 | 35.0 |
| Et-Trypsin | 100 | 100 | 93.9 | 79.7 | 69.7 | 43.0 | 40.0 |

* Enzyme concentration: 50 μg/ml for all the enzymes except pancreatin, which was 375 μg/ml.

EXAMPLE 13

The disinfecting efficacy of the cleaning and disinfecting methods of the present invention was evaluated by determining the rate and extent of kill achieved with the multi-purpose solution prepared from the Example 2A and 2B compositions. The multi-purpose solution was tested against *Serratia marcescens, Staphylococcus aureus, Pseudomonas aeruginosa, Candida albicans* and *Fusarium solani*. The test procedures and results are described below.

The following procedure was used:

A 0.1 mL volume of inoculum ($10^8$ colony forming units/mL) was first added to a 10 mL volume of the disinfecting solution of Example 2B, followed by the addition of 2 drops (1 drop equals about 30–40 μL using a "Droptainer") of the liquid enzyme composition of Example 2A. A similarly inoculated 10 mL volume of the disinfecting solution of Example 2B was used as a control. The solutions were maintained at room temperature throughout the test. Each microorganism and test solution was tested individually. Sets of four replicate (n = 8) samples were tested for each organism.

At selected time intervals of 1, 2, 3, 4, 6, 24 and 168 hours, a 1 mL volume of the inoculated test solution containing *Serratia marcescens, Staphylococcus aureus, Pseudomonas aeruginosa, Candida albicans* and *Fusarium solani* was removed and appropriate serial dilutions were made in sterile 0.9% sodium chloride solution dilution blanks. Pour-plates were prepared with soybean-casein digest agar containing 0.07% Asolectin and 0.5% Polysorbate 80. At Time 0, a 1.0 mL volume of the saline control was removed and serial dilution pour-plates were prepared using the same recovery medium and dilution blanks. The Time 0 saline control count was used as the initial count. The pour-plates were incubated at 30°–35° C. for appropriate incubation periods. The number of surviving organisms at each time interval was then determined. The test results, expressed as log reductions, are presented in Table 8, below.

TABLE 8

Disinfecting Efficacy of a Multi-Purpose Solution of the Present Invention

| Microorganism | Time (hours) | Log Reduction |
|---|---|---|
| C. albicans | 1 | 0.8 |
| | 2 | 0.9 |
| | 3 | 1.0 |
| | 4 | 1.1 |
| | 6 | 2.6 |
| | 24 | 5.6 |
| | 168 | 6.0* |
| F. solani | 1 | 3.1 |
| | 2 | 3.8 |
| | 3 | 4.3 |
| | 4 | 5.1 |
| | 6 | 5.8* |
| | 24 | 5.8* |
| | 168 | 5.8* |
| P. aeruginosa | 1 | 4.8 |
| | 2 | 4.8 |
| | 3 | 5.3 |
| | 4 | 6.1* |
| | 6 | 6.1* |
| | 24 | 6.1* |
| | 168 | 6.1* |
| S. marcescens | 1 | 2.1 |
| | 2 | 2.6 |
| | 3 | 2.9 |
| | 4 | 3.3 |
| | 6 | 4.5 |
| | 24 | 4.9 |
| | 168 | 6.0* |
| S. aureus | 1 | 2.7 |
| | 2 | 3.0 |
| | 3 | 3.3 |
| | 4 | 3.4 |
| | 6 | 3.8 |
| | 24 | 6.0* |
| | 168 | 6.0* |

*Indicates that no survivors (less than 10 cfu/mL) were recovered

EXAMPLE 14

The following example illustrates the cleaning efficacy of a multi-purpose composition (Example 6) of the present invention. The cleaning efficacy was determined using the following protocol.

1. Physiosolical/Thermal Combination Model:
Each lens was first soaked in a 5 ml lysozyme solution (native or C14-labeled, 1.0 mg/ml in 0.05M phosphate buffer containing 0.9% sodium chloride, pH 7.4) at 37° C. for 24 hours, then removed to a saline solution (2 ml) and heated at 90° C. for 15 minutes.

2. Cleaning and Assessment of Lysozyme Deposits:
Each deposited lens was placed in a 5 ml of a test solution and agitated in a rotary shaker at room temperature overnight (usually >12 hours). The compositions tested were: 1) the Example 6 composition (Me-trypsin), 2) 1 drop of Example 3B (except Me-trypsin was replaced by trypsin) in 5 mL of the Example 2B composition and 3) 1 drop of SupraClens® Daily Protein Remover (pancreatin) in 5 mL of the Example 2B composition. After rinsing the lens by dipping three times in three consecutive 40 ml saline solution, the lens was subjected to extraction with a 5 ml ACN/TFA solution (acetonitrile/trifluoroacetic acid/water: 500/1/500 v/v) for at least 2 hours. No mechanical rubbing was applied to the cleaning regimen. Both the extract and the soaking solution were then assessed for lysozyme by the protein intrinsic fluorescence method using a fluorescence spectrophotometer (excitation wavelength is 280 nm, emission wavelength is 346 nm), or by a scintillation counter for the C14-lysozyme. The quantification of lysozyme was based on a lysozyme standard curve established using the same vehicle and instrumental setting used for the lens extract and lens soaking solution. The results are show in Tables 9–10.

TABLE 9

Cleaning Efficacy Using the Fluorescence Method

| | Lysozyme (μg/Lens) | | | |
|---|---|---|---|---|
| Enzyme | Hydrolysate | ACN/TFA Extract | Total | % Cleaning Efficacy |
| SupraClens ® | 146.35 | 43.76 | 190.10 | 77.0 |
| Trypsin | 233.45 | 83.92 | 317.40 | 73.6 |
| Methylated Trypsin | 201.45 | 72.90 | 274.35 | 73.4 |

TABLE 10

Cleaning Efficacy Using the C-14 Method

| | Lysozyme (μg/Lens) | | | | |
|---|---|---|---|---|---|
| Enzyme | Hydrolysate | ACN/TFA Extract | Lens | Total | % Cleaning Efficacy |
| SupraClens ® | 98.69 | 38.5 | 4.74 | 141.93 | 69.5 |
| Trypsin | 145.02 | 48.43 | 3.57 | 197.02 | 73.6 |
| Methylated Trypsin | 141.61 | 52.85 | 3.75 | 198.21 | 71.4 |

The invention in its broader aspects is not limited to the specific details shown and described above. Departures may be made from such details within the scope of the accompanying claims without departing from the principles of the invention and without sacrificing its advantages.

What is claimed is:

1. A two-compartment, sterile multi-purpose composition generating bottle assembly for use in cleaning, disinfecting, rinsing and storing a contact lens comprising:
   a) a bottle containing an aqueous composition;
   b) a sealed container comprising a break-away membrane and containing an enzyme composition containing an amount of Al-trypsin; and
   c) an anti-microbial agent in an amount effective to disinfect the lens;
   wherein the anti-microbial agent is included in either the aqueous composition or the enzyme composition, the container is secured to and partially within the bottle, forming an internally sterile, two-compartment bottle assembly and breaking away the membrane allows for sterile egress of the enzyme composition into the aqueous composition of the bottle, wherein a multipurpose composition may be formed containing an Al-trypsin in an amount effective to clean the lens and an amount of the anti-microbial agent effective to disinfect the lens.

2. A bottle assembly according to claim 1, wherein:
the container further comprises a housing, a plunger, a removable cap and a collar;
the housing comprises a hollow cylinder containing the enzyme composition, a securing means, external threads and the membrane covers one end of the cylinder of the housing;
the plunger comprises a hollow cylinder, a dispensing end, and a bevel opposite end;
the cap comprises internal threads; and
the bottle further comprises an open end, neck and a receiving means for receiving and securing the container;
wherein the plunger is received within the hollow cylinder of the housing, the cap covers the plunger dispensing end and the internal threads of the cap are engaged with external threads of the housing, and the container is received and secured over the open end and within the neck of the bottle, forming an air-tight bottle assembly.

3. A bottle assembly according to claim 1, wherein the enzyme composition further comprises a suitable liquid vehicle.

4. A bottle assembly according to claim 3, wherein the suitable liquid vehicle comprises a water-miscible organic molecule and water.

5. A bottle assembly according to claim 4, wherein the water-miscible organic molecule is a polyol.

6. A bottle assembly according to claim 5 wherein the polyol is selected from the group consisting of glycerol, 1,2-propane diol, 1,3-propane diol, and ethylene glycol.

7. A bottle assembly according to claim 6, wherein the enzyme composition further comprises an effective amount of a borate/boric acid compound and an effective amount of calcium ion.

8. A bottle assembly according to claim 7, wherein the enzyme composition comprises propylene glycol or glycerol in the amount of from 40–85% w/v, a borate/boric acid compound in the amount of from 0.5–2.0% w/v and a calcium ion concentration of from 10 to 45 millimolar.

9. A bottle assembly according to claim 7, wherein the alkyl trypsin is selected from the group consisting of methyl trypsin and ethyl trypsin.

10. A bottle assembly according to claim 9, wherein the enzyme composition comprises methyl trypsin, 50% w/v propylene glycol, 1.5% w/v sodium borate, 0.25% w/v calcium chloride and water.

11. A bottle assembly according to claim 9, wherein the enzyme composition comprises methyl trypsin, 50% w/v glycerol, 1.5% w/v sodium borate, 0.25% w/v calcium chloride and water.

12. A bottle assembly according to claim 9, wherein the enzyme composition comprises methyl trypsin, 50% w/v PEG-400, 25% w/v glycerol, 1.5% w/v sodium borate, 0.25% w/v calcium chloride and water.

13. A bottle assembly according to claim 1, wherein the anti-microbial agent is polyquaternium-1.

14. A bottle assembly according to claim 1, wherein the aqueous composition comprises polyquaternium-1, boric acid, sorbitol, sodium chloride, sodium citrate, Tetronic 1304, disodium edetate, AMP-95, MAPDA, sodium hydroxide, hydrochloric acid and water; and the enzyme composition further comprises boric acid, propylene glycol, calcium chloride and water.

15. A bottle assembly according to claim 9, wherein the aqueous composition comprises:
about 0.001% w/v of polyquaternium-1;
about 0.6% w/v of boric acid;
about 1.2% w/v of sorbitol;
about 0.65% w/v of sodium citrate;
about 0.1% w/v of sodium chloride;
about 0.05% w/v of Tetronic 1304;
about 0.05% w/v of disodium edetate;
about 0.45% w/v of AMP-95;
about 0.0005% w/v of MAPDA; and water; wherein the composition is adjusted to pH 7–8 with sodium hydroxide and hydrochloric acid.

16. A method of preparing a sterile multi-purpose composition which comprises:
employing a two-compartment bottle assembly, said bottle assembly comprising:
a) a bottle containing an aqueous composition;
b) a sealed container comprising a break-away membrane and containing an enzyme composition containing an amount of an Al-trypsin; and
c) an anti-microbial agent;
wherein the anti-microbial agent is included in either the aqueous composition or the enzyme composition, and the container is secured to and partially within the bottle, forming an internally sterile, two-compartment bottle assembly;
breaking away the membrane and allowing the enzyme composition of the container to egress into the aqueous composition;
mixing the enzyme composition and aqueous composition together; and
forming a multi-purpose composition containing an Al-trypsin in an amount effective to clean the lens and an anti-microbial agent in an amount effective to disinfect the lens.

17. A method according to claim 16, wherein:
the container further comprises a housing, a plunger, a removable cap and a collar;
the housing comprises a hollow cylinder containing the enzyme composition, a securing means, external threads wherein the membrane covers one end of the cylinder of the housing;
the plunger comprises a hollow cylinder, a dispensing end, and a bevel opposite end;
the cap comprises internal threads; and
the bottle further comprises an open end, neck and a receiving means for receiving and securing the container;
wherein the plunger is received within the hollow cylinder of the housing, the cap covers the plunger dispensing end and the internal threads of the cap are engaged with external threads of the housing, and the container is received and secured over the open end and within the neck of the bottle, forming an air-tight bottle assembly.

18. A method according to claim 17, wherein the Al-trypsin is selected from the group consisting of methyl trypsin and ethyl trypsin.

19. A method according to claim 18, wherein the enzyme composition further comprises 50% w/v propylene glycol, 1.5% w/v sodium borate, 0.25% w/v calcium chloride and water.

20. A method according to claim 18, wherein the enzyme composition further comprises 50% w/v glycerol, 1.5% w/v sodium borate, 0.25% w/v calcium chloride and water.

21. A method according to claim 18, wherein the enzyme composition further comprises 50% w/v PEG-400, 25% w/v glycerol, 1.5% w/v sodium borate, 0.25% w/v calcium chloride and water.

22. A method according to claim 18, wherein the anti-microbial agent is polyquaternium-1.

23. A method according to claim 18, wherein the aqueous composition comprises polyquaternium-1, boric acid, sorbitol, sodium chloride, sodium citrate, Tetronic 1304, disodium edetate, AMP-95, MAPDA, sodium hydroxide, hydrochloric acid and water; and the enzyme composition further comprises boric acid, propylene glycol, calcium chloride and water.

24. A method according to claim 18, wherein the aqueous composition comprises:

about 0.001% w/v of polyquaternium-1;
about 0.6% w/v of boric acid;
about 1.2% w/v of sorbitol;
about 0.65% w/v of sodium citrate;
about 0.1% w/v of sodium chloride;
about 0.05% w/v of Tetronic 1304;
about 0.05% w/v of disodium edetate;
about 0.45% w/v of AMP-95;
about 0.0005% w/v of MAPDA; and water; wherein the composition is adjusted to pH 7–8 with sodium hydroxide and hydrochloric acid.

25. A method of cleaning and disinfecting a contact lens which comprises:

preparing a sterile multi-purpose composition by employing a two-compartment bottle assembly comprising:
 a) a bottle containing an aqueous composition;
 b) a sealed container comprising a break-away membrane and containing an enzyme composition containing an amount of an Al-trypsin; and
 c) an anti-microbial agent;
wherein the anti-microbial agent is included in either the aqueous composition or the enzyme composition, and the container is secured to and partially within the bottle, forming an internally sterile, two-compartment bottle assembly;
breaking away the membrane and allowing the enzyme composition of the container to egress into the aqueous composition;
mixing the enzyme composition and aqueous composition together;
forming a multi-purpose composition containing an Al-trypsin in an amount effective to clean the lens and an anti-microbial agent in an amount effective to disinfect the lens;
dispensing the multi-purpose composition into a receptacle; and
soaking the lens in the multipurpose composition of the receptacle for a time sufficient to clean and disinfect the lens.

26. A method according to claim 25, wherein:

the container further comprises a housing, a plunger, a removable cap and a collar;
the housing comprises a hollow cylinder containing the Al-trypsin composition, a securing means, external threads wherein the membrane covers one end of the cylinder of the housing;
the plunger comprises a hollow cylinder, a dispensing end, and a bevel opposite end;
the cap comprises internal threads; and
the bottle further comprises an open end, neck and a receiving means for receiving and securing the container;
wherein the plunger is received within the hollow cylinder of the housing, the cap covers the plunger dispensing end and the internal threads of the cap are engaged with external threads of the housing, and the container is received and secured over the open end and within the neck of the bottle.

27. A method according to claim 26, wherein the Al-trypsin is selected from the group consisting of methyl trypsin and ethyl trypsin.

28. A method according to claim 27, wherein the enzyme further composition comprises 50% w/v propylene glycol, 1.5% w/v sodium borate, 0.25% w/v calcium chloride and water.

29. A method according to claim 27, wherein the enzyme composition further comprises 50% w/v glycerol, 1.5% w/v sodium borate, 0.25% w/v calcium chloride and water.

30. A method according to claim 27, wherein the enzyme composition further comprises 50% w/v PEG-400, 25% w/v glycerol, 1.5% w/v sodium borate, 0.25% w/v calcium chloride and water.

31. A method according to claim 25, wherein the anti-microbial agent is polyquaternium-1.

32. A method according to claim 25, wherein the aqueous composition comprises polyquaternium-1, boric acid, sorbitol, sodium chloride, sodium citrate, Tetronic 1304, disodium edetate, AMP-95, MAPDA, sodium hydroxide, hydrochloric acid and water; and the enzyme composition further comprises boric acid, propylene glycol, calcium chloride and water.

33. A method according to claim 27, wherein the aqueous composition comprises:

about 0.001% w/v of polyquaternium-1;
about 0.6% w/v of boric acid;
about 1.2% w/v of sorbitol;
about 0.65% w/v of sodium citrate;
about 0.1% w/v of sodium chloride;
about 0.05% w/v of Tetronic 1304;
about 0.05% w/v of disodium edetate;
about 0.45% w/v of AMP-95;
about 0.0005% w/v of MAPDA; and water; wherein the composition is adjusted to pH 7–8 with sodium hydroxide and hydrochloric acid.

* * * * *